(12) United States Patent
Eknoian et al.

(10) Patent No.: US 7,901,696 B2
(45) Date of Patent: Mar. 8, 2011

(54) COSMETIC DEVICE COMPRISING DISCRETE ELEMENTS

(75) Inventors: Michael W. Eknoian, Warren, NJ (US); Robert A. Brennan, Jr., Mercerville, NJ (US); Raymond Ip, Plainsboro, NJ (US); John F. Poccia, III, Monmouth Beach, NJ (US)

(73) Assignee: J&J Consumer Companies, Inc., Skillman, NJ (US)

( * ) Notice: Subject to any disclaimer, the term of this patent is extended or adjusted under 35 U.S.C. 154(b) by 1503 days.

(21) Appl. No.: 11/263,169

(22) Filed: Oct. 31, 2005

(65) Prior Publication Data

US 2007/0098749 A1 May 3, 2007

(51) Int. Cl.
*A61K 9/00* (2006.01)

(52) U.S. Cl. ........................................ 424/400

(58) Field of Classification Search .................. None
See application file for complete search history.

(56) References Cited

U.S. PATENT DOCUMENTS

| | | |
|---|---|---|
| 389,296 A | 9/1888 | Greeley |
| 488,393 A | 12/1892 | Jewett |
| 681,324 A | 8/1901 | Hubbell |
| 4,155,870 A | 5/1979 | Jorgensen |
| 4,190,550 A | 2/1980 | Campbell |
| 4,240,760 A | 12/1980 | Levine |
| 4,335,185 A | 6/1982 | Adelman et al. |
| 4,374,175 A | 2/1983 | Tanaka |
| 4,525,411 A | 6/1985 | Schmidt |
| 5,221,506 A | 6/1993 | Dulin |
| 5,753,245 A | 5/1998 | Fowler et al. |
| 5,817,713 A | 10/1998 | Pappas et al. |
| 5,910,476 A | 6/1999 | Kinsman et al. |
| 5,937,874 A | 8/1999 | Guay et al. |
| 6,190,079 B1 | 2/2001 | Ruff |
| 6,352,948 B1 | 3/2002 | Pike et al. |
| 6,376,072 B1 | 4/2002 | Evans et al. |
| 6,818,603 B2 | 11/2004 | Aleles et al. |
| 2002/0022691 A1 | 2/2002 | Wang et al. |
| 2007/0098749 A1 | 5/2007 | Eknoian et al. |

FOREIGN PATENT DOCUMENTS

| | | | |
|---|---|---|---|
| EP | 1 393 717 A | | 3/2004 |
| EP | 1393717 A1 | * | 3/2004 |
| EP | 1 502 944 A | | 2/2005 |
| GB | 1288805 | | 9/1972 |
| RU | 2086620 | | 8/1997 |
| WO | WO 01/11003 A | | 2/2001 |
| WO | WO 2004/056955 A | | 7/2004 |

OTHER PUBLICATIONS

"Kuralon K-II" (trademark) Kuraray Co.,Ltd, publicly available prior to Aug. 14, 2002.

Package copy for "Loofah Exfoliating Soap", publicly available prior to Aug. 14, 2002.

\* cited by examiner

*Primary Examiner* — Robert A Wax
*Assistant Examiner* — Melissa S Mercier

(57) ABSTRACT

A cosmetic device comprising a solid or semi-solid cosmetic composition comprising a plurality of discrete elements is provided. The discrete elements each comprise a water soluble core surrounded by an erodible shell. The cosmetic composition may be a cleansing composition. The discrete elements may form a matrix.

35 Claims, No Drawings

COSMETIC DEVICE COMPRISING DISCRETE ELEMENTS

BACKGROUND OF THE INVENTION

Cosmetic bars have been used over the years to deliver many benefits to the skin. Cosmetic bars containing ingredients such as cocoa butter have been used to moisturize or protect the skin. More conventionally, bars containing soap and moisturizers have been used to cleanse and condition the skin. The bars have several problems associated with them. In particular, they are very slippery when wet. Cleansing bars tend to slip out of the consumer's hand during use in the shower or bath. The consumer then has to bend over or kneel down to pick up the cleansing bar from the floor of the shower.

Additionally, it is somewhat awkward to apply soap with a washcloth or sponge since it involves the use of two separable articles, one being extremely slippery when wet and tending to slide from the user's hands quite easily. Wrapping the washcloth around the soap may be a temporary solution but it is not completely satisfactory. Similarly, making a pouch in the sponge to contain the bar of soap leaves the sponge permanently saturated with the soap and slimy after its initial use. Sewing a bar of soap between two plies of washcloth likewise produces an article that is permanently slimy after use.

Others have tried to extend the life of a cosmetic or cleansing bar that is typically fragile when reduced to a sliver. The sliver will often break or become hand to handle. Solutions to these problems may include the incorporation of hair, sponges, fibers, etc. Examples of such disclosures are described in U.S. Pat. Nos. 681,324; 389,296; 488,393; and 5,221,506.

Skin cleansing compositions having abrasive particles incorporated as scrubbing aids are known in the art. For example, LOOFAH Exfoliating Soap is a commercially available soap bar from Earth Therapeutics. The soap bar has small particles of a chopped up loofah or puff dispersed throughout.

U.S. Pat. No. 6,818,603 describes a cleansing bar comprising (a) a cleansing composition; and (b) a plurality of discrete elements having a length to diameter ratio of from about 50 to 1 to about 1,000,000 to 1. The discrete elements may be fibers, filaments, particles, and mixtures thereof. In addition, the discrete elements may comprise monocomponent or multicomponent elements, including core-sheath structures. Such a device is useful for exfoliating the skin while cleansing. However, during its use, discrete elements, such as fibers exposed to the user's skin, trap hair and other debris, resulting in an unpleasant or unsanitary appearance. Subsequent washes exacerbate the problem.

Accordingly, a need still exists for a cosmetic device that provides exfoliation in a more sanitary and efficient manner. An improvement of the cleansing bar described in the '603 patent is disclosed herein, namely the use of discrete elements comprising a water soluble core surrounded by an erodible shell. A cosmetic device, whether for cleansing or otherwise, comprising such discrete elements provides a mechanism for removal of discrete elements from the cosmetic device. As discrete elements are exposed at the surface of the device, their erodible shells are abraded or dissolved with use. The water soluble cores are in turn exposed and fall away from the device.

SUMMARY OF THE INVENTION

The present invention provides a cosmetic device comprising a solid or semi-solid cosmetic composition comprising a plurality of discrete elements, said discrete elements each comprising a water soluble core surrounded by an erodible shell.

The invention also provides a method of forming a cosmetic device comprising the steps: (a) combining a flowable cosmetic composition with discrete elements each comprising a water soluble core surrounded by an erodible shell; and (b) allowing the combination of step (a) to form a solid or semi-solid.

The invention also provides a cosmetic device comprising a solid or semi-solid cosmetic composition comprising a matrix of discrete elements comprising a water soluble core surrounded by an erodible shell.

Finally, the invention provides a method of forming a cosmetic device comprising the steps: (a) combining a flowable cosmetic composition with a matrix of discrete elements comprising a water soluble core surrounded by an erodible shell; and (b) allowing the combination of step (a) to form a solid or semi-solid.

DETAILED DESCRIPTION OF THE INVENTION

As used herein the term "cosmetic" shall include conditioning, moisturizing, cleansing, or any other treatment that is applicable to the skin of the human body. Accordingly, the cosmetic device may be used to deliver any such treatment to the skin.

The cosmetic device comprises a cosmetic composition and discrete elements, either individual or in the form of a matrix. The finished cosmetic device may be a liquid, solid or semi-solid (including gel).

Cosmetic Composition

The cosmetic composition may be selected for example from moisturizing compositions, cleansing compositions, or any composition that may provide a benefit to the skin.

In one embodiment, the cosmetic composition is a cleansing composition. Suitable cleansing compositions are solid or semi-solid at room temperature. Examples of useful cleansing compositions include, but are not limited to, fatty acid soaps, including glycerin soaps, synthetic detergents and mixtures thereof. Solid cleansing compositions are extensively taught in Soap Technology for the 1990's, the contents of which are incorporated herein by reference. It is desirable that the cleansing composition be flowable.

In one embodiment of the invention, the cleansing composition comprises glycerin soap. Examples of glycerin soaps useful in the present invention include but are not limited to those disclosed in U.S. Pat. Nos. 4,405,492 and 4,879,063, the disclosures of which are hereby incorporated by reference.

Examples of suitable fatty acid soaps include soaps derived from hydrocarbon chain lengths of from approximately 10 to 22 (including carboxyl carbon) and may be saturated or unsaturated. The soap may be, for example, the sodium salt, potassium salt, ammonium salt, triethanolammonium salt and mixtures thereof.

Suitable synthetic detergents include those known in the art for the desired purpose. Examples of detergents useful for personal cleansing include the isethionates, sarcosinates, and glyceryl ether sulfonates which may be pure chain length variants or those derived from commercial oils such as coconut oil.

Numerous other detergents are appropriate for this invention. These include anionic acyl sarcosinates, methyl acyl taurates, N-acyl glutamates, alkyl sulfosuccinates, alkyl phosphate esters, ethoxylated alkyl phosphate esters, trideceth sulfates, protein condensates, mixtures of ethoxylated alkyl sulfates and alkyl amine oxides, betaines, sultaines and mixtures thereof. Included are the alkyl ether sulfates with 1 to 12 ethoxy groups, especially ammonium and sodium lauryl ether sulfates. Alkyl chains for these other detergents are $C_8$-$C_{22}$, preferably $C_{10}$-$C_{18}$. Alkyl glucosides and methyl glucoside esters are preferred mild nonionics, which may be mixed with other mild anionic or amphoteric surfactants in the compositions of this invention.

In one embodiment, the cleansing composition may comprise the following ingredients:

|  | % w/w |
| --- | --- |
| Propylene Glycol | 32.6 |
| Glycerin | 12.6 |
| Sodium Hydroxide Solution (50%) | 8.6 |
| Stearic Acid | 10.1 |
| Myristic Acid | 10.1 |
| Lauric Acid | 8.1 |
| Water ($H_2O$) | 4.0 |
| Sodium Lauryl Sulfate | 4.0 |
| Lauryl Methyl Gluceth-10 Hydroxypropyldimonium Chloride | 4.0 |
| Cocamidopropyl Betaine | 5.6 |
| Micro Titamium Dioxide | 0.3 |
| TOTAL | 100.0 |

In another embodiment, the cleansing composition comprises these ingredients:

|  | % w/w |
| --- | --- |
| Sodium Cocoyl Isethionate and Stearic Acid | 59.9 |
| Stearic Acid | 36.7 |
| Aminomethyl Propanol | 3.4 |
| TOTAL | 100.0 |

In yet another embodiment, the cleansing composition comprises a "flexible soap" composition as follows:

|  | % w/w |
| --- | --- |
| Water | 33.59 |
| Ca-Iota Carrageenan | 0.30 |
| Potassium Chloride | 0.70 |
| Sodium Laureth Sulfate | 24.88 |
| Kappa Carrageenan | 1.20 |
| Sodium Cocoyl Isethionate | 1.88 |
| Glycerin | 36.95 |
| Phenoxyethanol | 0.50 |
| TOTAL | 100.000 |

In another embodiment, the cosmetic composition is a moisturizing composition. For example, one moisturizing composition comprises the following ingredients:

|  | w/w % |
| --- | --- |
| Isopropyl Palmitate | 50 |
| Proprietary Polyamide | 15 |
| Cocamidopropyl Betaine | 5 |
| Sodium Lauryl Sulfate | 10 |
| Polyethyleneglycol 400 | 10 |
| Dimethicone | 10 |
| TOTAL | 100 |

Optional ingredients conventionally used in cosmetic compositions may be incorporated into the cosmetic device of this invention. These ingredients include, but are not limited to, perfumes/fragrances, preservatives, colorants, dyes, anti-caking agents, and personal care ingredients, including, but are not limited to, skin and hair care ingredients.

Examples of suitable personal care ingredients useful in the present invention include but are not limited to safe and effective amounts of: humectants, sunscreen actives, skin soothers, anti-irritants, anti-inflammatories, emollients, conditioning agents, moisturizers, deodorants, anti-perspirants, artificial tanning agents, antimicrobial agents, anti-acne agents, anti-wrinkle agents, anti-skin atrophy agents, skin firming agents, anti-itch agents, anti-fungal agents, topical anesthetics, skin tone evening agents, active natural ingredients, agents for minimizing the appearance or retarding regrowth of unwanted hair, skin texture modifiers, and additional cleansing agents.

Emollients function by their ability to remain on the skin surface or in the stratum corneum to act as lubricants, to reduce flaking, and to improve the skin appearance. Typical emollients include fatty esters, fatty alcohols, mineral oil, polyether siloxane copolymers and the like. Examples of suitable emollients include, but are not limited to, polypropylene glycol ("PPG")-15 stearyl ether, PPG-10 cetyl ether, steareth-10, oleth-8, PPG-4 lauryl ether, vitamin E acetate, PEG-7 glyceryl cocoate, lanolin, and combinations thereof. Vitamin E acetate, PEG-7 glyceryl cocoate and combinations thereof are preferred.

Examples of suitable humectants include polyhydric alcohols. Suitable polyhydric alcohols include, but are not limited to, glycerol (also known as glycerin), polyalkylene glycols, alkylene polyols and their derivatives, including propylene glycol, dipropylene glycol, polypropylene glycol, polyethylene glycol and derivatives thereof, sorbitol, hydroxypropyl sorbitol, hexylene glycol, 1,3-dibutylene glycol, 1,2,6,-hexanetriol, ethoxylated glycerol, propoxylated glycerol and mixtures thereof.

Suitable skin soothers include, but are not limited to, panthenol, bisabolol, allantoin, aloe, and combinations thereof.

Suitable conditioning agents include, but are not limited to, dimethicone propyl PG-betaine, dimethicone copolyols, polyquaternium-10, guar, guar derivatives, and combinations thereof. Suitable anti-acne active ingredients include, but are not limited to, salicylic acid, sulfur, lactic acid, glycolic acid, pyruvic acid, urea, resorcinol, N-acetylcysteine, retinoic acid, benzoyl peroxide, octopirox, triclosan, azelaic acid, phenoxyethanol, phenoxypropanol, flavinoids, derivatives thereof, and combinations thereof. Salicylic acid and benzoyl peroxide are preferred.

The optional ingredients may be incorporated into the cleansing composition by means known in the art. Alternatively, the optional ingredients may be incorporated into or coated onto the discrete elements by means known in the art, provided that the optional ingredients sufficiently adhere to the discrete elements until incorporated into the cosmetic device. As used herein "coated" means surface coating and/or at least partially impregnating the discrete element. The optional ingredients may be incorporated into or coated onto the discrete element or encapsulated into other components by means known in the art, for example, by treatment with an appropriate solution, suspension or slurry of the ingredient in an appropriate liquid, followed by drying by conventional means. See, for example, U.S. Pat. Nos. 4,335,185; 6,376,072; and 6,420,047, the disclosures of which are hereby incorporated by reference.

Discrete Elements

The discrete elements may be made from a wide range of materials, both natural and synthetic. Suitable discrete elements include, but are not limited to, fibers, filaments, particles, and mixtures thereof.

The discrete elements comprise a water soluble core surrounded by an erodible shell. As used herein, "water-soluble" means that the cores disperse, disintegrate, or dissolve in water via chemical degradation and/or hydrolysis and/or solvation. Suitable materials for water soluble cores include, but are not limited to, polyethylene oxide ("PEO"), blends of PEO and polypropylene as taught in United States Patent Application 2002/022691 A1, hereby incorporated by reference. Other examples include polylactic acid fibers sold under the tradename LACTRON® by Kanebo, polysaccharides sold under the tradename LYSORB® available from Lysac Technologies Inc., and polyvinyl alcohol such as those sold under the tradename KURALON K-II available from Kuraray Co., Ltd. and any natural soluble starch type materials. Mixtures of these are also contemplated.

As used herein, the term "erodible" means the shells degrade or disintegrate via mechanical, thermal, or chemical means. For instance, the erodible shells may be made of water insoluble or water permeable material. Suitable materials for use in the erodible shell include stearyl alcohol, fatty alcohols, esters, and fatty acids. Water-insoluble materials also include acetate rayon and cellulose (which are relatively supple when wetted with water), polyamides such as poly(hexamethylene adipamide), polycaproamide and/or copolymers thereof; polyesters, such as poly(ethylene terephthalate); poly(hexahydro-p-xylylene terephthalate), and/or copolymers; polyolefins, such as polypropylene and polyethylene; polyurethanes, polycarbonates, polyacetals, polyacrylics, vinyl polymers, vinylidene polymers, nylon, and the like. Mixtures of these are also contemplated.

"Erodible" may also mean that the shells are water soluble but at a rate that is equal to or slower than the rate at which the cores dissolve. Suitable materials for water soluble shells include, but are not limited to, polyethylene oxide ("PEO"), blends of PEO and polypropylene as taught in U.S. Patent Application 2002/022691 A1. Other examples include polylactic acid fibers sold under the tradename LACTRON® by Kanebo, polysaccharides sold under the tradename LYSORB® available from Lysac Technologies Inc., and polyvinyl alcohol such as those sold under the tradename KURALON K-II available from Kuraray Co., Ltd and any natural soluble starches. Mixtures of these are also contemplated.

In one embodiment, the discrete elements have a length to diameter ratio of from about 50 to 1 to about 100,000 to 1. In a preferred embodiment, the discrete elements have a length to diameter ratio of from about 100 to 1 to about 25,000 to 1, more preferably from about 500 to 1 to about 5,000 to 1. As used herein the term "diameter" means the diameter of a circular cross section of the discrete element, or in cases where the discrete element does not have a circular cross section, such as with some natural fibers or synthetic multi-lobal fibers, the term "diameter" means the diameter of a circle equal in area to the actual measured cross sectional area of the discrete element.

The length of the discrete element varies depending on the benefit desired. Generally, the length varies from about 0.125 to about 5.0 inches, more preferably from about 0.5 to about 3 inches and most preferred from about 1 to about 1.5 inches.

In another embodiment, the discrete elements are formed into a matrix, for example a nonwoven web. The discrete elements may be in the form of fibers, strands, or filaments, etc. The discrete elements in matrix can either be random (i.e., randomly aligned) or they can be carded (i.e. combed to be oriented in primarily one direction). Furthermore, the matrix can be composed of a combination of layers of random and carded discrete elements. The type, diameter and length of the discrete elements may vary according to the desired use. For example, relatively thick discrete elements may be used in a cosmetic device for washing the hands while thin and more supple discrete elements may be used in a cosmetic device used as a bath soap. Methods of making matrices such as nonwoven webs are well known in the art. Such methods include, but are not limited to, air-laying, water-laying, melt-blowing, spinbonding, or carding processes. The resulting substrate, regardless of its method of production or composition, is then subjected to at least one of several types of bonding operations to anchor the individual discrete elements together to form a self-sustaining web. The matrix can also be prepared by a variety of processes including hydroentanglement, thermal bonding, and combinations of these processes.

In one embodiment, the cosmetic composition may be colored and the discrete elements may also colored. The discrete elements may be a color that is the same or different from the color of the cosmetic composition. Alternatively, the discrete elements may be a mixture of discrete elements having different colors.

In another embodiment, the discrete elements may include super absorbent polymer (SAP) fibers as described in U.S. Pat. Nos. 4,374,174; 5,817,713; 6,376,072, the disclosures of which are hereby incorporated by reference.

When the discrete element is a fiber, the denier may vary depending on the benefit desired. Typically, the denier ranges from about 0.025 to 25, more preferably from about 1.5 to about 15, and most preferred from about 3 to about 9.

The amount of the discrete elements in the cosmetic device will also vary based upon the desired benefit. In one embodiment, the amount of discrete elements will range from about 0.01 percent to about 20 percent by weight, more preferably from about 0.1 to 10%, most preferably from about 0.5 to about 5%, based on the total weight of the cosmetic device.

The cosmetic device may be made by any of the conventional methods known in the art. These methods include but are not limited to hot pour and extrusion methods, the particulars of which are known by those skilled in the soap art.

In one embodiment, the cosmetic device may be prepared by heating a cosmetic composition to a temperature at which it flows, i.e., above its melting point (for example, for glycerin soap composition about 70° C. to about 130° C.). The composition is mixed with discrete elements (or matrix, if that is used). The discrete elements may be mixed with the cosmetic composition, for example by agitation, and then the mixture is cooled into a solid or semi-solid form.

Optional ingredients like perfume, skin care ingredients, colorants, and sensates may be added.

EXAMPLES

Example 1

In a suitably sized container, 10.0 g of poly(vinyl alcohol) fibers (Kuralon KII WN from Kuraray LTD) were blended with 50.0 g molten stearyl alcohol at 80° C. for 10 minutes. The fibers were then cooled to room temperature and pulled apart to form free fibers of PVA coated with stearyl alcohol.

Two 500 mL beakers filled with hot water (60° C.) were placed side by side. The coated fibers from Example 1 were added to one beaker. The uncoated fibers were added to the second beaker. Immediately the uncoated fibers dissolved while the coated fibers did not dissolve.

Example 2

The following soap base was prepared and made molten by heating to 80° C.:

|  | % w/w |
|---|---|
| Propylene Glycol | 32.6 |
| Glycerin | 12.6 |
| Sodium Hydroxide Solution (50%) | 8.6 |
| Stearic Acid | 10.1 |
| Myristic Acid | 10.1 |
| Lauric Acid | 8.1 |
| Water (H$_2$O) | 4.0 |
| Sodium Lauryl Sulfate | 4.0 |
| Lauryl Methyl Gluceth-10 Hydroxypropyldimonium Chloride | 4.0 |
| Cocamidopropyl Betaine | 5.6 |
| Micro Titanium Dioxide | 0.3 |
| TOTAL | 100.0 |

The fibers from Example 1 were then placed into a soap mold and the above composition was added to form a cosmetic device according to the invention. The fibers remained intact and did not dissolve when contacted by the molten soap base.

We claim:

1. A cosmetic device comprising a solid or semi-solid cosmetic composition comprising a plurality of discrete elements, said discrete elements each comprising a water soluble core surrounded by an erodible shell.

2. The cosmetic device of claim 1, wherein the cosmetic composition is a cleansing composition.

3. The cosmetic device of claim 1, wherein the cosmetic composition is a moisturizing composition.

4. The cosmetic device of claim 1, wherein the cosmetic composition is hot pourable.

5. The cosmetic device of claim 1, wherein the water soluble core comprises a material selected from the group consisting of polyethylene oxide, polyethylene oxide-propylene blends, polylactic acid, polysaccharides, polyvinyl alcohol, and mixtures thereof.

6. The cosmetic device of claim 1, wherein the erodible shell comprises a material selected from the group consisting of stearyl alcohol, fatty alcohols, esters, fatty acids and mixtures thereof.

7. The cosmetic device of claim 1, wherein the erodible shell is water soluble at a rate equal to or slower than the rate of water solubility of the core and comprises a material selected from the group consisting of polyethylene oxide, polyethylene oxide-propylene blends, polylactic acid, polysaccharides, polyvinyl alcohol, and mixtures thereof.

8. The cosmetic device of claim 1 comprising about 0.01 percent to about 20 percent by weight of discrete elements.

9. A method of forming a cosmetic device comprising the steps:
   a) combining a flowable cosmetic composition with discrete elements each comprising a water soluble core surrounded by an erodible shell; and
   b) allowing the combination of step (a) to form a solid or semi-solid.

10. The method of claim 9, further comprising agitating the combination of step (a).

11. The method of claim 9, further comprising extruding the combination of step (a).

12. The method of claim 9, further comprising molding the combination of step (a).

13. The method of claim 9, wherein the cosmetic composition is a cleansing composition.

14. The method of claim 9, wherein the cosmetic composition is a moisturizing composition.

15. The method of claim 9, wherein the cosmetic composition is hot pourable.

16. The method of claim 9, wherein the water soluble core comprises a material selected from the group consisting of polyethylene oxide, polyethylene oxide-propylene blends, polylactic acid, polysaccharides, polyvinyl alcohol, and mixtures thereof.

17. The method of claim 9, wherein the erodible shell comprises a material selected from the group consisting of stearyl alcohol, fatty alcohols, esters, fatty acids and mixtures thereof.

18. The method of claim 9, wherein the erodible shell is water soluble at a rate equal to or slower than the rate of water solubility of the core and comprises a material selected from the group consisting of polyethylene oxide, polyethylene oxide-propylene blends, polylactic acid, polysaccharides, polyvinyl alcohol, and mixtures thereof.

19. The method of claim 9 wherein the cosmetic device comprises about 0.01 percent to about 20 percent by weight of discrete elements.

20. A cosmetic device comprising a solid or semi-solid cosmetic composition comprising a matrix of discrete elements comprising a water soluble core surrounded by an erodible shell.

21. The cosmetic device of claim 20, wherein the cosmetic composition is a cleansing composition.

22. The cosmetic device of claim 20, wherein the cosmetic composition is a moisturizing composition.

23. The cosmetic device of claim 20, wherein the cosmetic composition is hot pourable.

24. The cosmetic device of claim 20, wherein the water soluble core comprises a material selected from the group consisting of polyethylene oxide, polyethylene oxide-propylene blends, polylactic acid, polysaccharides, polyvinyl alcohol, and mixtures thereof.

25. The cosmetic device of claim 20, wherein the erodible shell comprises a material selected from the group consisting of stearyl alcohol, fatty alcohols, esters, fatty acids and mixtures thereof.

26. The cosmetic device of claim 20, wherein the erodible shell is water soluble at a rate equal to or slower than the water solubility of the core and comprises a material selected from the group consisting of polyethylene oxide, polyethylene oxide-propylene blends, polylactic acid, polysaccharides, polyvinyl alcohol, and mixtures thereof.

27. A method of forming a cosmetic device comprising the steps:
   a) combining a flowable cosmetic composition with a matrix of discrete elements comprising a water soluble core surrounded by an erodible shell; and
   b) allowing the combination of step (a) to form a solid or semi-solid.

28. The method of claim 27, further comprising molding the combination of step (a).

29. The method of claim 27, wherein the cosmetic composition is a cleansing composition.

30. The method of claim 27, wherein the cosmetic composition is a moisturizing composition.

31. The method of claim 27, wherein the cosmetic composition is hot pourable.

32. The method of claim 27, wherein the water soluble core comprises a material selected from the group consisting of polyethylene oxide, polyethylene oxide-propylene blends, polylactic acid, polysaccharides, polyvinyl alcohol, and mixtures thereof.

33. The method of claim 27, wherein the erodible shell comprises a material selected from the group consisting of stearyl alcohol, fatty alcohols, esters, fatty acids and mixtures thereof.

34. The method of claim 27, wherein the erodible shell is water soluble at a rate equal to or slower than the rate of water solubility of the core and comprises a material selected from the group consisting of polyethylene oxide, polyethylene oxide-propylene blends, polylactic acid, polysaccharides, polyvinyl alcohol, and mixtures thereof.

35. The method of claim 27 wherein the cosmetic device comprises about 0.01 percent to about 20 percent by weight of discrete elements.

* * * * *